United States Patent
Stutterheim et al.

(10) Patent No.: US 12,156,514 B2
(45) Date of Patent: Dec. 3, 2024

(54) EGG POSITIONING DEVICE

(71) Applicant: In Ovo Holding B.V., Leiden (NL)

(72) Inventors: Wil Marijn Stutterheim, Leiden (NL); Leonard Van Bommel, Leiden (NL); Wouter Sebastiaan Bruins, Leiden (NL); Edwin Dijksterhuis, Enschede (NL)

(73) Assignee: In Ovo Holding B.V., Leiden (NL)

( * ) Notice: Subject to any disclaimer, the term of this patent is extended or adjusted under 35 U.S.C. 154(b) by 196 days.

(21) Appl. No.: 17/792,197

(22) PCT Filed: Jan. 18, 2021

(86) PCT No.: PCT/NL2021/050029
§ 371 (c)(1),
(2) Date: Jul. 12, 2022

(87) PCT Pub. No.: WO2021/145772
PCT Pub. Date: Jul. 22, 2021

(65) Prior Publication Data
US 2023/0045391 A1     Feb. 9, 2023

(30) Foreign Application Priority Data
Jan. 17, 2020   (NL) .................................... 2024701

(51) Int. Cl.
*A01K 43/00* (2006.01)
*A01K 45/00* (2006.01)
*G01N 33/08* (2006.01)

(52) U.S. Cl.
CPC ............ *A01K 43/00* (2013.01); *A01K 45/007* (2013.01); *G01N 33/085* (2013.01)

(58) Field of Classification Search
CPC ...... A01K 43/00; A01K 45/007; A01K 43/04; A01K 45/00; A01K 2227/30;
(Continued)

(56) References Cited

U.S. PATENT DOCUMENTS

| 6,176,199 B1 | 1/2001 | Gore et al. |
| 6,510,811 B1 | 1/2003 | Gore et al. |

(Continued)

FOREIGN PATENT DOCUMENTS

| EP | 1804574 B1 | 6/2013 |
| EP | 2786656 A1 | 10/2014 |

(Continued)

*Primary Examiner* — Michael P Stafira
(74) *Attorney, Agent, or Firm* — Harness, Dickey & Pierce, P.L.C.

(57) ABSTRACT

The present disclosure relates to a computer-controlled system for non-invasively identifying the location of the air cell of an egg and determining a preferred extraction point relative to the position of the air cell of the egg, the system having an egg manipulator to hold and orient one or more eggs in a defined position; a candling unit with one or more light sources and one or more detectors; a system configured to run an algorithm for determining the location of the air cell and the preferred extraction point; and a system for positioning the egg relative to an extractor or an egg opener or vice versa from their initial position to the preferred extraction point.

18 Claims, 6 Drawing Sheets

(58) Field of Classification Search
CPC ............ A01K 67/0275; A01K 2267/02; A01K 2217/05; A01K 2217/072; A01K 2267/03; G01N 33/085; G01N 33/08; G01N 1/34; G01N 1/10; G01N 30/72; G01N 33/6848; G01N 33/74; G01N 35/04; G01N 35/08; G01N 35/1009; G01N 35/1065; G01N 35/1095; G01N 2021/8854; G01N 21/27; G01N 21/85; G01N 21/8806; G01N 21/8851; G01N 21/95; G01N 2201/1042; G01N 25/72

See application file for complete search history.

(56) References Cited

U.S. PATENT DOCUMENTS

| | | | |
|---|---|---|---|
| 7,617,795 B2* | 11/2009 | Wolfe | A01K 45/007 |
| | | | 119/6.8 |
| 9,686,969 B2 | 6/2017 | Meissner et al. | |
| 2004/0107912 A1 | 6/2004 | Hebrank | |
| 2006/0038978 A1 | 2/2006 | Zweig et al. | |
| 2007/0024844 A1* | 2/2007 | Hebrank | G01N 33/085 |
| | | | 356/53 |
| 2015/0225208 A1* | 8/2015 | Suh | A47J 29/06 |
| | | | 414/811 |
| 2015/0327520 A1 | 11/2015 | Van De Zande | |
| 2017/0020115 A1 | 1/2017 | Suh et al. | |
| 2018/0196024 A1* | 7/2018 | Hurlin | A01K 43/00 |
| 2020/0187462 A1* | 6/2020 | Meter | A01K 45/007 |

FOREIGN PATENT DOCUMENTS

| | | |
|---|---|---|
| EP | 3497441 A1 | 6/2019 |
| JP | 2011-215015 A | 10/2011 |
| KR | 101138550 B1 * | 5/2012 |
| WO | 98/14053 A1 | 4/1998 |
| WO | 2019/007520 A1 | 1/2019 |
| WO | 2019/025323 A1 | 2/2019 |
| WO | WO-2019154493 A1 * | 8/2019 ............ A01K 43/00 |

* cited by examiner

EGG POSITIONING DEVICE

FIELD OF THE INVENTION

The present application provides a system for non-invasively identifying the location of the air cell of an egg and positioning the egg relative to an extracting device or vice versa based on the position of the air cell with minimal mechanical movement and user interaction.

BACKGROUND OF THE INVENTION

The allantois or allantoic sac is a portion of an avian egg that develops and then enlarges in the egg from about the $5^{th}$ to $13^{th}$ day, and thereafter is absorbed and diminishes in size until the egg is hatched. The allantoic sac functions as a respiratory surface, a calcium adsorbing tissue, a liquid waste receptacle for urine secreted by the mesonephros, and as a water reservoir to sustain later stage development of the embryo. The allantoic sac reaches its peak volume at about the $11^{th}$ day of incubation and begins to diminish in size after about the $13^{th}$ day. Since the allantoic sac essentially grows to surround the embryo, it normally exists as a relatively thin layer under the inner shell membrane which presents a difficult target for injection even during the period of maximum volume.

Avian eggs are injected with various substances for the production of vaccines or microorganisms or cells, to generate transgenic or chimeric birds, to decrease mortality rates of hatched chickens or to increase embryo growth rates of chickens. Sampling eggs on an industrial scale in order to monitor the status of the egg is a fairly recent development in the field. A number of industrial egg sampling systems and methods have been developed, including for instance those disclosed in EP-A-2786656, EP-A-1804574 and EP-A-3497441.

One method of sampling or injecting the allantois of an avian egg involves candling of individual eggs to locate the allantois, and then injecting or sampling the allantois by hand using a syringe. Injection into the allantois by hand has been practiced in the biological sciences for the purpose of culturing various microorganisms therein.

Efforts by the poultry industry to inject into the allantois using vertical downward injection through the large end of a vertically oriented egg by traversing the air cell and air cell membrane have been reported, but efforts to accomplish this on a large scale using conventional egg injection equipment have produced mixed results with a significant number of injections discharging into the air cell or the amnion instead of the allantois.

U.S. Pat. No. 6,176,199B1 discloses a method for large scale injecting and optionally sampling the allantois of an avian egg based on the duration of incubation of the egg, but does not disclose the use of an algorithm to determine the position of the allantois and also specifically avoids traversing the air cell of the egg with a probe or needle.

U.S. Pat. No. 9,686,969B2 discloses an injection system for injecting a substance into a specific location within an egg containing an avian embryo, which comprises mapping the x, y, z coordinates of embryonic structures to locate the specific injection location and moving the egg's pointed pole upwards to its injection position, but it does not teach or suggest to specifically target the allantois, to position the egg and/or extractor in a specific position relative to the air sac while intending to traverse the air sac with the extractor, nor to extract a sample from the egg.

U.S. 65/108,111B1 discloses a method for localizing the allantoic fluid of an avian egg in order for the fluid to be injected, sampled or assessed, but it does not comprise the use of a candling unit nor teach how to automatically determine the location of the allantois or the air cell of an individual egg.

US20180196024A1 discloses an automated method and an apparatus for determining the location of the air cell of an egg, which is held blunt-side up, by candling, optionally disinfecting the blunt side of the egg, and opening the egg shell.

Preferably, then a second candling may be performed after creating an opening in the eggshell, introducing a probe to obtain information on the sex of the embryo in the egg, using Raman or fluorescence spectroscopy, and the egg may be sealed afterwards.

Processing of a multitude of eggs or using a multitude of opening or sampling devices are not disclosed nor is the positioning of an egg towards an opening or sampling device. WO2019025323A1 discloses an automated method and an apparatus for determining the location of the air cell of an egg, using a thermal, MRI, ultrasound or EIT image to determine the location of the air cell. It is disclosed that a multitude of eggs can be imaged simultaneously and then a processing device and an opening device are positioned towards the eggs, and their position is adapted to allow for a suitably located eggshell penetration.

JP2011215015A discloses a method for determining the location of the air cell of an egg, and for determining if an embryo is alive, wherein a candling light and detector are both located at the blunt-side of the egg and preferably located in a light-sealed cup together with the blunt-side of the egg. The disclosure is silent about the positioning of an opening or injection device relative to the egg or vice versa, let alone a process for opening the egg, and also does not disclose the use of a multitude of devices or eggs.

Hence there remains a need for an automated system that can specifically and accurately determine the position of the allantois and/or air cell of an egg, and position the egg relative to an extractor, in order to accurately take samples from the egg by traversing the air cell of the egg.

SUMMARY OF THE INVENTION

In a first aspect, the present invention provides an automated, preferably computer-controlled system for non-invasively identifying the location of the allantois of an egg and positioning the egg relative to an extractor based on the position of the allantois of the egg, comprising: an egg manipulator to hold and orient one or more eggs in a defined position; a candling unit comprising one or more light sources and one or more detectors; a system which is configured to run an algorithm for determining the location of the air cell of the egg and the preferred extraction point; and a system for positioning the egg relative to an extractor or an egg opener or vice versa from their initial position to the preferred extraction point.

In a second aspect, the present invention relates to a method for non-invasively identifying the location of the air cell of an egg and positioning the egg relative to an extractor based on the position of the air cell of the egg, using the system according to the invention.

In a further aspect, the subject system relates to a system wherein the egg holder or tray having an egg immobilization means employs either a vacuum or a suitable mechanical means to fix the position of the egg or plurality of eggs.

In yet a further aspect, the subject system relates to a system where in the extraction position the distance from the extractor to the allantois of the egg is 0 to 30 mm.

The present invention also relates to the process of non-invasively identifying the location of the allantois of an egg and positioning the egg relative to an extractor based on the position of the allantois of the egg, comprising the steps of:

a. fixing the egg or a plurality of eggs;
b. candling the egg;
c. determining the location of the allantois of the egg using an algorithm; and
d. positioning the egg or a plurality of eggs relative to an extractor or a plurality of extractors or vice versa from their initial position to their injection position where the trajectory of the extractor to the allantois of the egg is linear.

DETAILED DESCRIPTION OF THE INVENTION

A "tray" is understood to mean a type of product created and designed in various colors, materials, mechanisms, shapes, sizes and styles used to hold and protect a specific number of eggs.

"Candling" is a common method used in embryology to study the growth and development of an embryo inside an egg. The term "candling" is understood here to mean using a light source or otherwise suitable emitter of electromagnetic waves of sufficient strength directed at an egg enabling the detection of any structures inside an egg, preferably at least of the air cell. This may be done by shining such waves through the egg and collating the data at an opposite side of an egg, or by illuminating the egg and collating data on reflected and/or diverted wave data.

A "candling unit" herein is a system comprising one or more light sources and one or more detectors, which generates candling data on the egg structures.

An "extractor" is understood to mean an object capable of removing a gas, fluid or solid sample from another object.

An "egg" herein refers to avian eggs, preferably to eggs of chicken (*Gallus Gallus domesticus*).

The "egg axis" is also commonly known as the major axis of the egg. The major axis spans the greatest possible distance between the tip of the pointed side of the egg and the base of the blunt side of the egg.

The term "fixing" herein refers to fixation of an object, here egg, in a spatial position that allows to determine the location of the components and organs in the egg.

The term "extraction point" refers to a point or space located on the shell of an egg where eventually an extractor can enter without causing harm, or disrupting the further development of the embryo in the egg.

An "egg manipulator" herein refers to a device configured to hold and secure an egg in a predefined position, wherein the means for securing comprises a system that is configured to move between an egg securing position and an egg releasing position.

An "egg rotator" is understood to mean a device capable of moving or causing to move an egg in any degree of a circle or circular motion around the egg axis or a center point of the egg which is in a horizontal line with the rotator. The egg rotator can be a part of the egg manipulator wherein the egg is held in an egg securing position and the egg manipulator together with the secured egg is movable in any degree of a circle around the egg axis or a center point of the egg which is in a horizontal line with the rotator. In another embodiment the egg is placed on an egg rotator which comprises a bearing, preferably a ball bearing or roller bearing.

The present invention relates to an automated system for non-invasively identifying the location of the air cell and/or the allantois of an egg and determining a preferred extraction point relative to the position of the air cell of the egg. The system comprises the following parts:

a. an egg manipulator to hold and orient one or more eggs in a defined position;
b. a candling unit comprising one or more light sources and one or more detectors;
c. a system which is configured to run an algorithm for determining the location of the air cell and/or the allantois of the egg and the preferred extraction point, preferably on the basis of the candling data, and
d. a system for positioning the egg relative to an extractor or an egg opener or vice versa from their initial position to the preferred extraction point.

In a preferred configuration of the system and method according to the invention a multitude of openers or extractors are used simultaneously in order to increase the speed and efficiency of the sampling or injecting. A multitude of openers or extractors is also more efficiently cleaned or disinfected by for example external spraying of a cleaning or disinfecting substance or internal simultaneous flushing with a cleaning or disinfecting substance, wherein optionally the substance is added in parallel to all openers or extractors.

Moving, rotating and/or positioning one or more individual eggs relative to one or a multitude of openers and/or extractors to allow extraction at each individual preferred extraction point requires less energy than moving, rotating and/or positioning the multitude of openers or extractors relative to one or more individual eggs. The multitude of openers and/or extractors is preferably part of a sampling unit, which is a much more complex and larger system than an egg holding system. Altering the position of a relatively simple egg holding system is thus simpler and requires less energy and/or computational intensity than altering the position of a system comprising a multitude of openers and/or extractors.

This is in particular effective when the openers or extractors are in a defined position, preferably in a fixed defined position relative to each other, such as in a sampling array. When the openers or extractors are in a fixed position relative to each other, the resulting trajectories and/or orientations of the openers and/or extractors towards the one or more eggs are also defined and fixed accordingly. A fixed position relative to each other has the advantage of providing constant and predictable trajectories and/or orientations of the multitude of openers or extractors, which greatly facilitates (automated) positioning of the one or more individual eggs relative to the openers or extractors. Applicants found that by simply rotating an egg around the egg axis permits to achieve a very high accuracy in determining an extraction point where an extractor can enter the eggshell without disrupting vital membranes, and with the necessary precision to be able to draw a sample from the desired fluid, in particular the allantois, and not egg white, egg yolk or even blood or tissue samples.

Accordingly, the present invention also relates to an automated system for non-invasively identifying the location of the air cell of an egg and determining a preferred extraction point relative to the position of the air cell of the egg, the system comprising:

a. an egg manipulator to hold and orient one or more eggs in a defined position;
b. a candling unit comprising one or more light sources and one or more detectors;
c. a system configured to determine the location of the air cell of the egg and the preferred extraction point; and
d. a system for positioning one or more eggs relative to a multitude of extractors and/or egg openers to allow extraction at a preferred extraction point.

Preferably, the individual extractors and/or egg openers of the multitude of extractors and/or egg openers are next to each other.

Preferably, the individual extractors and/or egg openers of the multitude of extractors and/or egg openers are attached to each other.

Preferably, the individual extractors and/or egg openers of the multitude of extractors and/or egg openers are fixed relative to each other.

Preferably, the orientation of each of the individual extractors and/or egg openers of the multitude of extractors and/or egg openers is similar.

Preferably, the trajectory of each of the individual extractors and/or egg openers of the multitude of extractors and/or egg openers towards the one or more eggs is similar.

The individual extractors and/or egg openers of the multitude of extractors and/or egg openers are preferably positioned adjacent to each other, preferably spaced apart such that each extractor and/or egg opener's position corresponds to an egg, thereby forming a, preferably movable, assembly. Equally, egg manipulators and egg candling units are preferably arranged in assemblies comprising a multitude of devices, each positioned in relation to an egg. Preferably the eggs are positioned in crates or other holding devices commonly used in the field that comprise a multitude of eggs in an orderly fashion in rows.

The individual extractors and/or egg openers of the multitude of extractors and/or egg openers can for example be oriented in a straight horizontal, vertical or diagonal line relative to each other or in a single or multiple curved line. The position of the individual extractors and/or egg openers of the multitude of extractors and/or egg openers relative to each other is preferably related to the position of the one or more eggs. More preferably, the positions are similar or identical. For example, a conveyor belt holding five or ten eggs at an equal distance to each other and in a straight alignment would preferably be matched with a position of individual extractors and/or egg openers of five or ten extractors and/or egg openers at the same distance to each other and in the same alignment as the five or then eggs are positioned. Of course, this may also be done with a wider array, such as e.g. 20, 30 or 100 eggs at a time.

The distance between each of the individual eggs or egg holders is thus similar to the distance between each of the individual extractors and/or egg openers of the multitude of extractors and/or egg openers.

Preferably, the one or more eggs is the same number as the multitude of extractors and/or egg openers.

A multitude is understood to mean at least two. The optimal multitude of extractors and/or egg openers depends on for example the available physical space and desired speed of the automated system and thus there is no theoretical maximum. In practice, the multitude ranges preferably of from 2 to 400, more preferably 2 to 200, 2 to 100, 4 to 10, 4 to 6, or 5.

"Similar" herein is understood to mean essentially identical; for example about the same shape, about the same angle, about the same direction or about the same proportion, or at an essentially identical angle, direction or proportion.

Preferably, the egg manipulator employs a means exerting vacuum or a mechanical means to hold the egg in the predefined position, or a combination thereof. Preferably, the egg manipulator comprises two or more, preferably three or four, movable objects configured to move into or out of contact with the egg to respectively hold the egg or release the egg. The egg manipulator preferably also comprises an egg rotator for rotating the egg, preferably around a central axis defined by the pinnacle of the egg and the centre of the blunt end. Preferably, the egg rotator comprises a bearing allowing for a rotation around the central axis, to avoid friction, while still maintaining the egg in the predefined position.

Egg manipulator and egg rotator may be integrally formed, or separate units. Preferably an egg rotator may be positioned underneath an egg, more preferably allowing the egg to rest on the rotator. Preferably, an egg manipulator may be positioned above the egg. Preferably, the egg manipulator comprises a system to position the egg at a distance of from 0 to 30 mm from the light source of the candling unit for candling.

During candling, the egg may advantageously be positioned to be in contact with a spacer object located in between the egg and the light source. This spacer member spaces each egg at a predetermined distance from the light source.

Preferably, the spacer object or member comprises a lumen with two openings placed between the egg and the light source, to permit the light to reach the egg through the lumen. It may be in direct contact with the light source, or it may advantageously be made integral with the light source.

Advantageously, the spacer object comprises a bearing permitting rotation of the egg when in contact with the spacer, so that when an egg is rotated, the spacer is rotated along, without transferring the rotation to the light source.

The light source, or light emission sources, may preferably comprise an incandescent or luminescent light source emitting electromagnetic radiation, such as a halogen, gas-discharge, laser or light-emitting diode light source, in particular a high-intensity discharge, fluorescent, neon, argon, sulphur, metal-halide, plasma, xenon-flash, laser diode, chemical laser, gas laser, ion laser, solid-state laser light source. In a preferred embodiment, the light source is configured to emit light in a wavelength of from 300-2500 nm. According to some aspects, the light source may comprise a light emitting diode (LED) configured to emit light from the visible portion, or the infrared portion of the electromagnetic spectrum. However, aspects of the present disclosure are not limited to the use of LEDs or infrared radiation. Various types of light sources may be utilized without limitation such as, for example, a laser diode source or a solid-state excitation source. The light source may emit light that is pulsed, time-sliced or modulated so as to avoid measurement errors caused by light emitted from adjacent light sources.

The detector or detector assembly comprising a plurality of detectors for receiving electromagnetic radiation.

The system 100 may further include a detector assembly having a plurality of light sources and detectors for receiving electromagnetic radiation, such as light transmitted through, or reflected by the egg during the candling operation.

In some instances, the detector assembly may be positioned opposite the light source assembly in axial alignment so as to form a plurality of light source/detector pairs capable of evaluating eggs in a high throughput manner. Each light source may contain light sources at one or more wavelengths so that the associated detector at each position may measure opacity at one or more wavelengths.

To measure several wavelengths with a single detector, light from the different light sources may be time-sliced or modulated to separate the opacity measurement at each wavelength. Preferably, the detector is positioned relative to the light source such that the detector can detect an image of the egg via light originating from the light source, however preferably not through the egg, but light source and detector are positioned at the same side.

Advantageously, the light source is positioned between the egg and the detector. The detector may suitable be positioned at an angle of from 0-45° relative to a light ray originating from the light source.

According to a preferred embodiment of the invention, the detector may comprise a camera unit for capturing images of the illuminated upper portion of the egg, arranged such that the central egg revolution axis is substantially vertical, preferably by means of a light source arranged over the egg substantially on the revolution axis of the egg, and the acquisition of an image of the upper portion of the illuminated egg by a camera, arranged in the vicinity of the light source, preferably above the light source. The image acquisition axis of the camera may form an angle ranging between 0 and 70° with a reference plane that is perpendicular to the central axis of the egg.

Advantageously, the camera may acquire at one, preferably more than one image of the illuminated egg/The images may then advantageously be analysed to determine the location of various components in the egg. Preferably, the system also comprises a computing unit configured to run an algorithm to determine the location of the allantois of the egg, and preferably, the system is also configured to run an algorithm for determining the location of the allantois, vasculature, yolk or embryo of the egg, based on the detected candling data, in particular images of the illuminated egg. The system further preferably also is configured to run an algorithm directed at excluding unfertilized eggs or eggs containing dead, undeveloped or underdeveloped embryos.

Based on the candling data which allows the system to determine at least the positions of the air cell and the allantois, the system further preferably determines the location of the preferred extraction point on the egg.

This preferred extraction point is a point selected on the eggshell, where the eggshell meets a point on a line parallel to the central egg axis, typically at a distance of from 2-7 mm from the central axis of the egg, and at the side where the air cell of the egg is positioned closest to the shell of the egg. More preferably, the location of the preferred extraction point comprises a point on the shell of the egg on a line parallel to the egg axis and having a distance of from 4-5 mm directly from the central axis of the egg from the lowest point of the air cell of the egg closest to the shell of the egg, when the egg is positioned with the blunt side upwardly.

The system further preferably comprises an eggshell opening member, further referred to as "opener" herein. The system further is configured and operable to position the egg such that egg and egg opener meet at the preferred extraction point, or at least to position egg and opener relative to each other in the trajectory of the opener towards the preferred extraction point.

The system further preferably is configured to position the egg or the egg opener at an angle to each other of from 15-90° relative to the central egg axis. The system further preferably is configured to position the egg into contact with the extractor or vice versa in the preferred extraction point or to position the egg or the extractor in the trajectory of the opener towards the preferred extraction point. The system further preferably is configured to position the egg or the extractor at an angle to each other of from 0-45° relative to the egg axis.

At a preferred extraction point, the extractor preferably traverses the air cell of the egg and enters the allantois of the egg by a distance of from 0.5-9 mm, preferably 3 mm.

The extractor further preferably comprises at least one hollow elongated object, preferably more than one hollow elongated objects attached to, or incorporated in the extractor. The hollow elongated object is preferably configured to hold or transfer a sample from the egg. The hollow elongated object preferably comprises one or more openings at the proximate end. The one or more openings are preferably located at a distance of from 0-15 mm from the distal end of the hollow elongated object. The extractor and hollow elongated object having one or more openings is preferably formed or selected such that, from a preferred extraction point, the hollow elongated object may traverse the air cell of the egg, and enter the allantois of the egg to a depth of from 0.5 to 9 mm, preferably about 3 mm.

The hollow elongated object is preferably of an essentially right or oblique cylinder shape, and preferably has an inner diameter of from 0.07 to 4.40 mm and an outer diameter of from 0.18 to 5.17 mm. More preferably, the hollow elongated object has an inner diameter of from 0.1 to 0.5 mm and an outer diameter of from 0.2 to 0.75 mm. The hollow elongated object may comprise at least one cutting edge, the cutting edge formed by intersecting planar surfaces, the surfaces converging towards a distal end, the angle of convergence comprising an angle of slope of from 120 to 179°, preferably of from 30° to 100°.

Preferably, the hollow elongated object may have a multi-bevelled point, comprising a cannula having a lumen, the lumen extending from a first end of the cannula and having an opening defined through the first end, the first end terminating in a point with a plurality of discrete planar bevels contiguously bounding the opening, wherein one of the plurality of discrete bevels is located furthest from the point. It preferably may have a length shorter than any of the other ones of the plurality of discrete bevels. The actual shape of the hollow elongated object, or sampling needle is not critical, provided that it may be employed to extract samples from the allantois.

The hollow elongated object advantageously may be a needle configured to draw material, in particular allantoic fluid, from the egg, as would be understood by those skilled in the art. For example, the needle may have a blunt tip and an axially-extending lumen that terminates at an aperture formed within a portion of the needle adjacent the tip. Material can be drawn into the lumen via the aperture upon subjecting the lumen to vacuum or reduced pressure.

The present invention also relates to a method for non-invasively identifying the location of the air cell and/or allantois of an egg and positioning the egg relative to an extractor based on the position of the air cell of the egg, using a system according to the present invention.

The method according to the invention relates to a method for non-invasively identifying the location of the air cell of an egg and determining a preferred extraction point relative to the position of the air cell of the egg, comprising the steps of:
  a. holding and orienting the egg in a defined position;
  b. candling the egg;
  c. determining the location of the air cell of the egg and the preferred extraction point, preferably using a system employing an algorithm translating the candling data into position data; and
  d. automatically positioning the egg relative to an extractor and/or an opener from the initial position, and
  e. opening the egg at the preferred extraction point.

Preferably, the method instead has a step d. which is automatically positioning one or more eggs relative to a multitude of extractors and/or openers from the initial position.

The automated method may include the following steps: a) providing at least one egg; b) subjecting the egg to a candling treatment to determine if the egg is fertile, and to determine the position of the air cell and allantois; c) opening the egg shell at a preferred extraction point; d) extracting a sample from the allantois through the preferred extraction point, and e) closing the shell to avoid further contact with the shell exterior, and optionally, f) subjecting the sampled materials to an analysis method.

The present invention also relates to a computer program product comprising instructions to cause the inventive system to execute the steps of the method. It further also relates to a computer-readable medium having stored thereon the computer program.

The present invention also relates to the use of the system disclosed herein, for the automated sampling of materials from eggs, in particular the allantois, which may suitably allow to determine a plethora of different properties and egg characteristics, including but not limited, to sex determination of the embryo in the egg or determining the viability of an embryo, or to determine e.g. the presence of a particular gene or allele of interest in the embryo. The invention will be further explained with reference to the non-limiting figures. Alternatively, dipstick methods using affinity compounds and/or luminescence, or PCR methods may be employed; alternatively, also Raman or hyperspectral analysis may be employed.

DETAILED DESCRIPTION OF THE FIGURES

Figure 1:
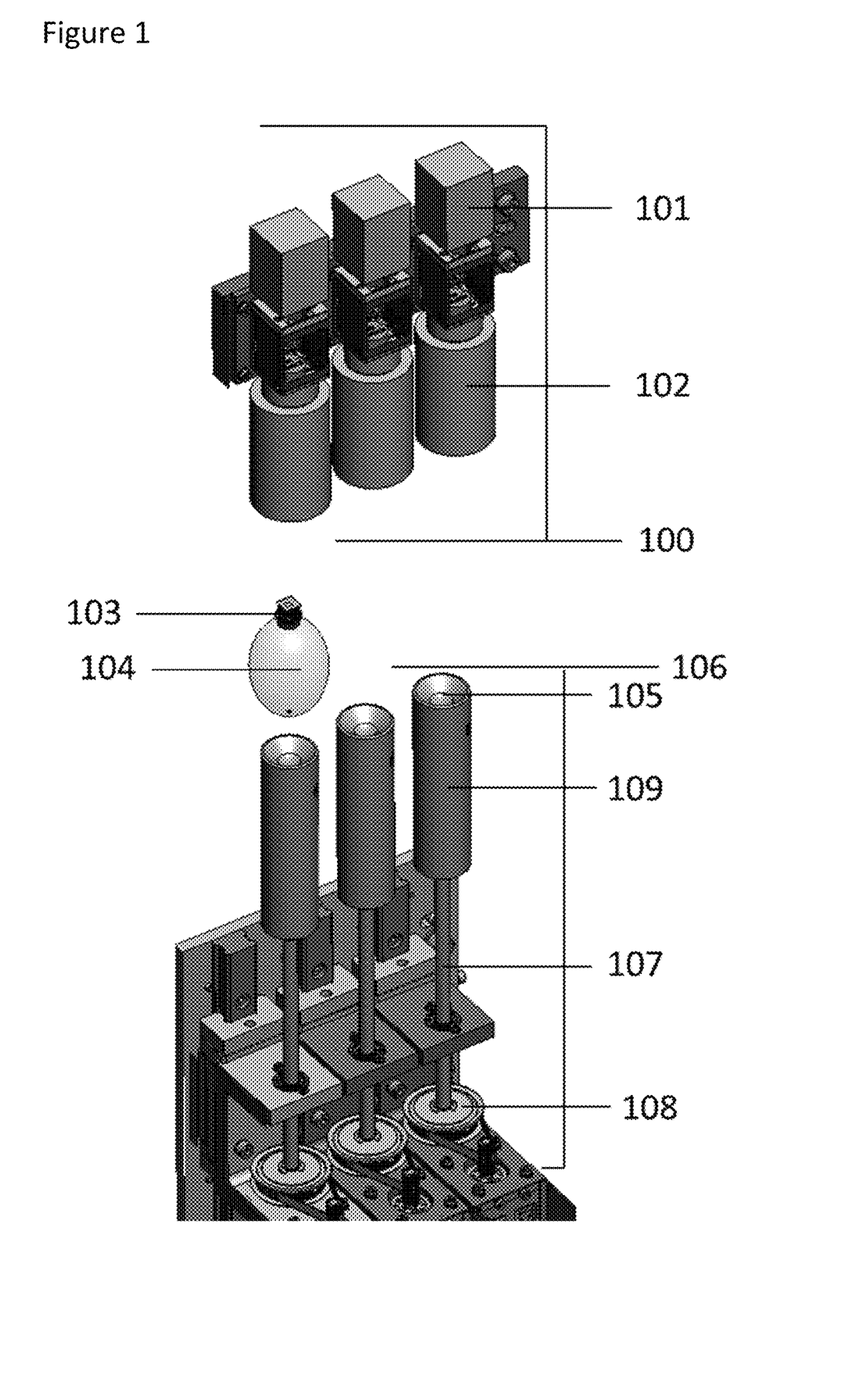
FIG. 1 shows a model of a device capable of holding one or more eggs, which is also capable of rotating the egg and/or positioning the egg relative to a candling unit.

FIG. 1 shows a model of a device capable of holding one or more eggs, which is also capable of rotating the egg and/or positioning the egg relative to a candling unit. An egg (104) is held in place by a vacuum or a mechanical means (105) of an egg manipulator (106). An extension (107) is configured to position the egg (104) towards a spacer object (103) in front of a candling unit (100), comprising one or more detectors and one or more lighting sources. An egg rotator (108) is configured to be able to rotate the egg manipulator (106) and the egg (104). The data obtained from the candling unit may advantageously be processed to determine the location of air cell and allantois, or vasculature and other characteristics.

Figure 2:
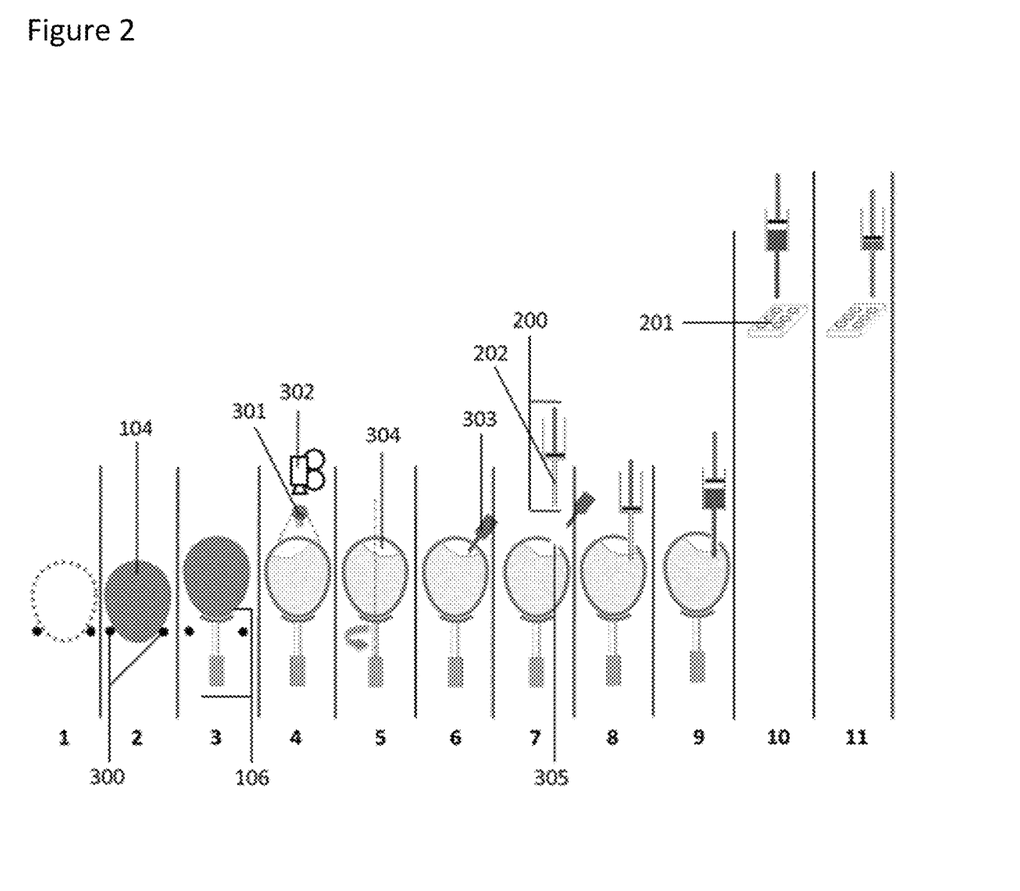
FIG. 2 shows a schematic overview of different steps of a system for taking one or more samples from one or more eggs.

FIG. 2 shows a schematic overview of different steps of a system for taking one or more samples from one or more eggs. In step 1 an empty egg holder or tray (300) is present. In step 2 an egg (104) is placed blunt side up on the egg holder or tray (300). In step 3 an egg manipulator (106) is configured to hold the egg securely and is configured to lift the egg from the egg holder or tray (300). In step 4 the egg (104) is positioned by the egg manipulator (106) in front of a candling unit comprising a light source (301) and a detector (302) and candled. In step 5 a system which is configured to run an algorithm for determining the location of the air cell (304) of the egg (104) and a preferred extraction point (305) directs the egg manipulator (106) to rotate the egg (104) based on the information gathered by the detector (302). In step 6 the egg (104) and/or an opener (303) are positioned relative to each other in order for the opener (303) and subsequently the extractor (200) to contact the preferred extraction point (305). The opener (303) opens the egg (104). In step 7 the opener (303) is retracted from the egg (104) and the extractor (200) comprising a hollow elongated object (202) is positioned above the preferred extraction point (305). In step 8 the hollow elongated object (202) of the extractor (200) passes the preferred extraction point (305), enters the egg (104) and traverses the air cell (304). The distal end of the hollow elongated object (202) enters the allantois or a different structure of the egg (104). In step 9 the extractor (200) removes a sample from the egg (104). In step 10 the extractor is removed from the egg (104) towards an instrument for holding comprising a multitude of sample containers (e.g. a microtiter plate) (201). In step 11 the extractor (200) ejects the sample in the microtiter plate (201).

Figure 3:
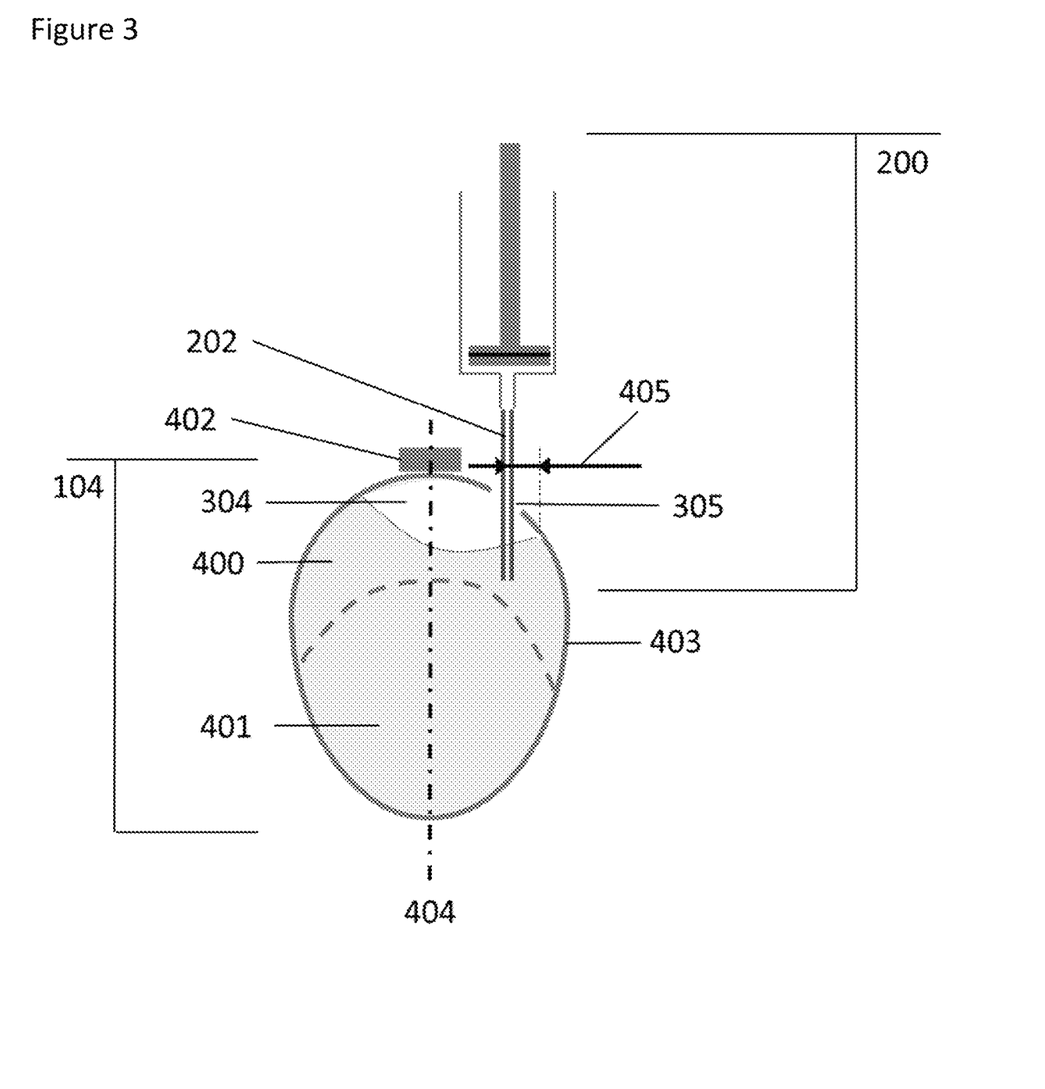
FIG. 3 shows a detailed schematic cross section of an extractor positioned in an egg at the moment before taking a sample.

FIG. 3 shows a detailed schematic cross section of an extractor positioned in a (chicken) egg at the moment before taking a sample. The hollow elongated object (202) of an extractor (200) has entered an egg (104) through a preferred extraction point (305) and traversed the air cell (304) in order to remove a sample from the allantois (400) of the egg (104) without entering any underlying anatomical structures (401). The blunt end of the egg (104) is positioned against an end stop (402). The location of the preferred extraction point (305) comprises a point on the shell (403) of the egg (104) on a line parallel to the egg axis (404) having a distance of from 2-7 mm directly towards the centre of the egg (104) from the lowest point of the air cell (304) of the egg (104) closest to the shell (403) of the egg (104) (i.e. the edge distance (405)), the egg (104) being blunt side up.

Figure 4:
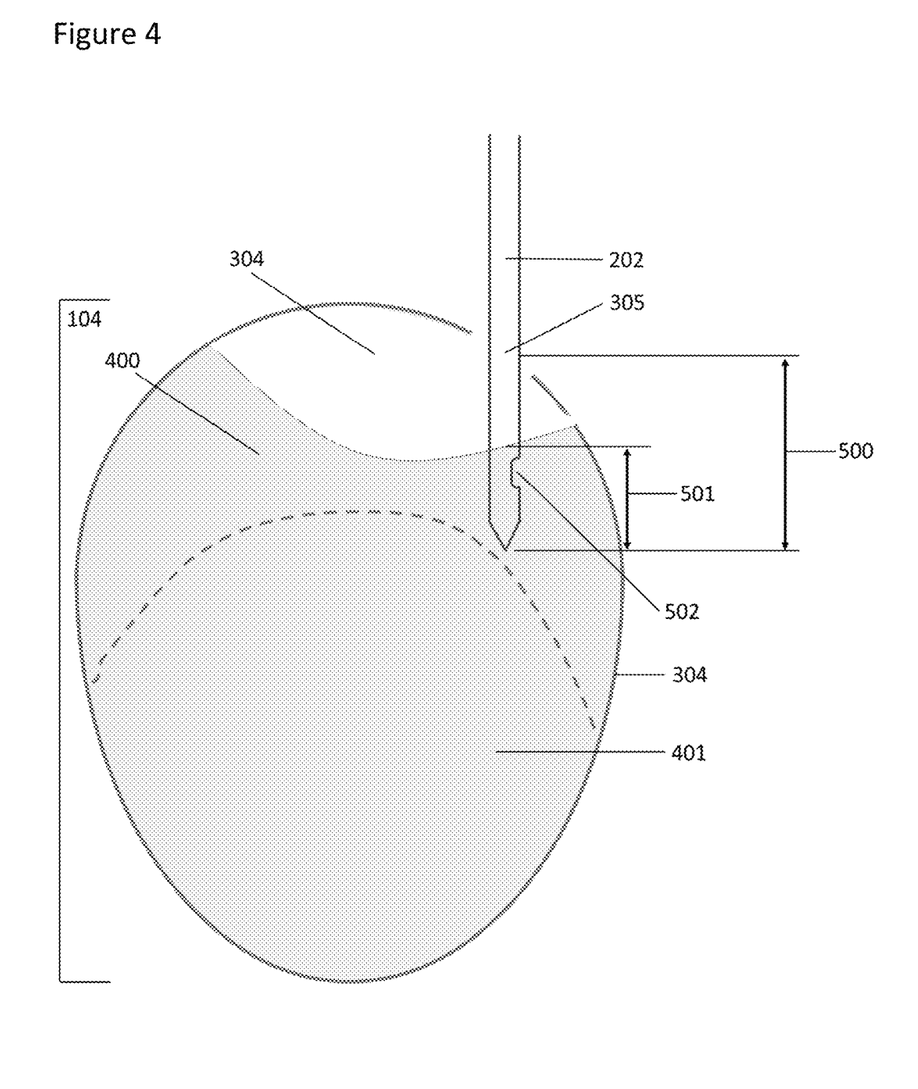
FIG. 4 shows a schematic cross section of a hollow elongated object of an extractor positioned in an egg.

FIG. 4 shows a schematic cross section of a hollow elongated object of an extractor positioned in an egg. The hollow elongated object (202) of an extractor (200) has entered an egg (104) through a preferred extraction point (305) and traversed the air cell (304) in order to remove a sample from the allantois (400) of the egg (104) without entering any underlying anatomical structures (401). The distance of which the hollow elongated object (202) has traversed through the egg (104) from the preferred extraction point (305) is termed the needle depth (500). The distance of which the hollow elongated object (202) has traversed the allantois (400) is termed the penetration depth (501). The hollow elongated object (202) comprises a lateral opening (502) configured to remove a sample from the allantois (400).

Figure 5:
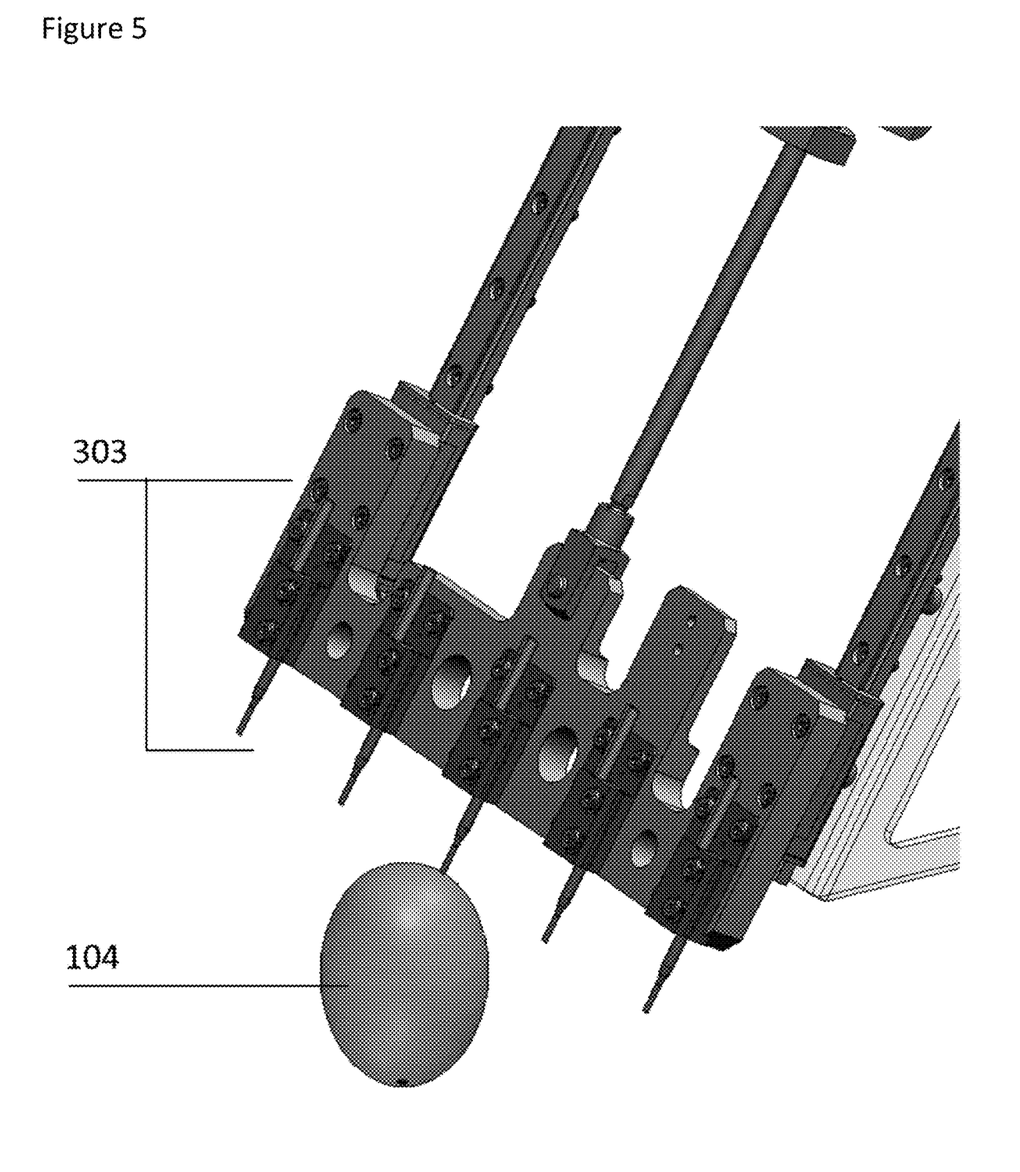
FIG. 5 shows a model for an apparatus containing several openers positioned relative to an egg.

FIG. 5 shows a model for an apparatus containing several openers positioned relative to an egg. An apparatus containing five openers is located at a specific angle relative to an egg (104) being blunt side up. A single opener is indicated by (303). In this model only one egg (104) is shown, but one to five eggs can be positioned in such a way that they are all simultaneously into contact with the distal end of the five openers (303). The openers are in a fixed position relative to each other. In order for all of the individual openers to be positioned simultaneously relative to an individual egg with respect to the trajectory of the opener towards the preferred extraction point of an individual egg it is necessary that the eggs are each individually positioned towards the opener and not vice versa.

Figure 6:
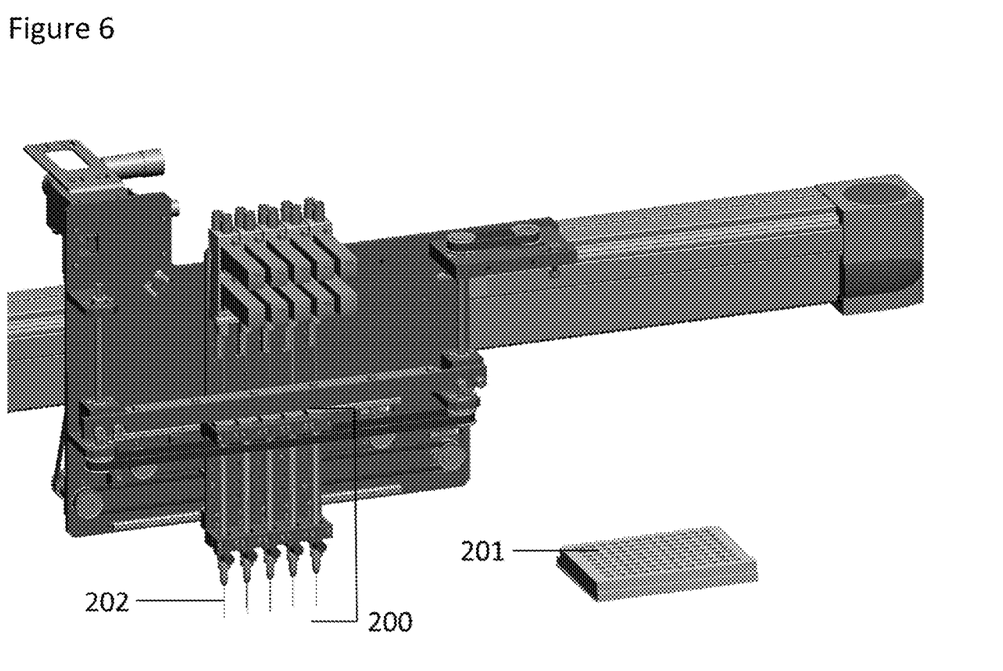
FIG. 6 shows a model for an apparatus containing several extractors, capable of moving the extractors from and to an instrument for holding comprising a multitude of sample containers.

FIG. 6 shows a model for an apparatus containing several extractors, capable of moving the extractors from and to an instrument for holding comprising a multitude of sample containers. The apparatus shown contains five extractors (200) each comprising a hollow elongated object (202). This model can move the extractors to and from a position above one or more eggs to and from an instrument for holding comprising a multitude of sample containers (e.g. a microtiter plate) (201). The extractors are in a fixed position relative to each other. In order for all of the individual extractors to be positioned simultaneously relative to an individual egg in the trajectory of the extractor through the preferred extraction point of an individual egg it is necessary that the eggs are each individually positioned towards the extractor and not vice versa.

The present system was shown to permit an automated sampling of large amounts of eggs in a relatively short period of time, thereby allowing to remove samples from fertilized eggs on an industrial scale.

The invention claimed is:

1. An automated system for non-invasively identifying the location of the air cell of an egg and determining a preferred extraction point relative to the location of the air cell, the system comprising:
   an egg manipulator to hold and orient one or more eggs in a defined position, wherein the egg manipulator comprises an egg rotator for rotating the egg;
   a candling unit comprising one or more light sources and one or more detectors, wherein the light source is position between the egg and the detector;
   a system configured to determine the location of the air cell and the preferred extraction point; and
   a system for positioning the egg relative to one or both of an extractor and/or an egg opener to allow extraction at a preferred extraction point.

2. The system according to claim 1, comprising a plurality of extractors and/or a plurality of egg openers.

3. The system according to claim 1, wherein the egg manipulator comprises a vacuum or a mechanical means to hold the egg in the position.

4. The system according to claim 1, wherein the egg manipulator comprises two or more movable objects configured to hold or release the egg.

5. The system according to claim 1, wherein the egg rotator comprises a bearing.

6. The system according to claim 1, wherein the light source comprises an incandescent or luminescent light source.

7. The system to according to claim 1, wherein the light source is configured to emit light in a wavelength in a range of from 300 to 2500 nm.

8. The system according to claim 1, further comprising a system configured to determine and exclude unfertilized eggs or eggs containing dead, undeveloped or underdeveloped embryos.

9. The system according to claim 1, wherein the preferred extraction point is at a point on a line parallel to a central egg axis and on a side of the egg where the air cell is closest to a shell of the egg.

10. A method for non-invasively identifying a location of an air cell of an egg and determining a preferred extraction point relative to the location of the air cell of the egg, the method comprising:
    holding and orienting the egg in a defined position;
    candling the egg using a light source positioned between the egg and a detector;
    determining the location of the air cell of the egg and the preferred extraction point using a system employing an algorithm configured to convert candling data into location data;
    rotating the egg;
    automatically positioning the egg relative to one or both of an extractor and an egg opener from an initial position, and
    opening the egg at the preferred extraction point.

11. The system according to claim 1, wherein the system configured to determine the location of the air cell and the preferred extraction point comprises a computing unit.

12. The system according to claim 11, wherein the computing unit is further configured to determine a location of one or more of an allantois, vasculature, yolk, and embryo of the egg.

13. The system according to claim 1, wherein the detector is positioned relative to the light source such that the detector can detect an image of the egg via light originating from the light source.

14. The system according to claim 13, wherein the detector can take a reflection and/or dispersion image of the illuminated egg.

15. The system according to claim 1, wherein the egg manipulator comprises a system to position the egg at a distance of from 0 to 30 mm from the light source of the candling unit for candling.

16. The system according to claim 1, further comprising a spacer object, wherein during candling the egg is positioned to be in contact with a spacer object, which is located in between the egg and the light source and spaces the egg at a predetermined distance from the light source.

17. The system according to claim 1, wherein the location of the preferred extraction point is determined at a point on the shell of the egg on a line parallel to the central egg axis at a distance of from 2 mm to 7 mm from the center of the egg axis at the lowest point of the air cell of the egg and closest to the shell of the egg, when the egg is positioned with the blunt side pointing upwardly.

18. The system according to claim 1, wherein the extractor is configured to, at the preferred extraction point, traverse the air cell of the egg and to enter the allantois of the egg to a depth of from 0.5 mm to 9 mm.

* * * * *